United States Patent [19]

Terano

[11] Patent Number: 4,659,570

[45] Date of Patent: Apr. 21, 1987

[54] PREPARATION CONTAINING STABILIZED PHYSIOLOGICALLY ACTIVE SUBSTANCE

[75] Inventor: Yoshitake Terano, Ikeda, Japan

[73] Assignee: Suntory Limited, Osaka, Japan

[21] Appl. No.: 727,261

[22] Filed: Apr. 25, 1985

[30] Foreign Application Priority Data

Apr. 26, 1984 [JP] Japan .................. 59-84990

[51] Int. Cl.[4] .................. A61K 45/02; C12P 21/00
[52] U.S. Cl. ............................. 424/85; 435/68
[58] Field of Search ............ 424/85; 435/68, 811; 260/112 R, 112 B

[56] References Cited

U.S. PATENT DOCUMENTS 4,147,772 4/1979 McAleer et al. .............. 424/89
4,465,622 8/1984 Nobuhara et al. ............. 424/85

FOREIGN PATENT DOCUMENTS 80879 8/1983 European Pat. App. .
102519 8/1980 Japan .

OTHER PUBLICATIONS

Derwent Abstract of Japanese Unexamined Published Patent Application No. 167518, 1983.

*Primary Examiner*—Blondel Hazel
*Attorney, Agent, or Firm*—Cushman, Darby & Cushman

[57] ABSTRACT

A preparation of stabilized physiologically active substance which is produced by incorporating a physically and chemically modified gelatin in a physiologically active substance made of basic protein or polypeptide, such as interferons, specially gamma-interferon.

5 Claims, No Drawings

PREPARATION CONTAINING STABILIZED PHYSIOLOGICALLY ACTIVE SUBSTANCE

FIELD OF THE INVENTION

The present invention relates to a preparation of stabilized physiologically active substance which is characterized by incorporating a modified gelatin in a physiologically active substance comprised of a basic protein or polypeptide. More particularly, the present invention relates to a stabilized preparation produced by incorporating a modified gelatin (to be described later in this specification) in a physiologically active substance made of a basic protein or polypeptide, such as alpha-interferon (IFN-$\alpha$), beta-interferon (IFN-$\beta$), gamma-interferon (IFN-$\gamma$), interleukin 2, lysozyme or an antibody complement (particularly its first component, Cl). The present invention is effective in producing stabilized preparations of interferons, especially IFN-$\gamma$.

PRIOR ART:

It has been proposed to stabilize interferons by incorporating anionic surfactants (Unexamined Published Japanese Patent Application No. 16752/1983) or antiviral nonionic surfactants (Unexamined Published Japanese Patent Application No. 77824/1983). But the so stabilized preperations are limited to external uses in the mouth, skin, rectum, vagina, urethra, eye, ear or nose and are not completely suitable for direct administration into the human body by, for example, intravenous injection. Human serum albumin has been proposed for use as a stabilizer for IFN-$\gamma$ preparations (Unexamined Published Japanese Patent Application No. 90514/1983). Human serum albumin is a metabolite of the human biological system and satisfies most of the requirements for use as a component in pharmaceutical preparations, such as no side effect in the human body, easy metabolism and elimination from the body, and no antigenicity. However, as will be described hereinafter, the limited resources and safety of human serum albumin prevent its extensive use in practical applications.

Human serum albumin is prepared from the human blood and the basic method of its production is the Cohn fractionation with cold ethanol that was developed in the 1940s (see, for example, Cohn et al.: Am. Chem. Soc. 68; 459–475, 1946). However, the use of cold ethanol causes denaturation and inactivation of a host of valuable and biologically active serum proteins. Furthermore, the Cohn process is complicated and time-consuming since it involves many steps of treatment and can be implemented only in a batch system. As a result, the higher structure of human serum albumin molecules may be destroyed or coagulations may occur. Later studies on the methods for separation and purification of human serum albumin include: (1) fractional precipitation by additionof a neutral salt such as sodium sulfate or a water-soluble polymer such as poly(ethylene glycol) (PEG); (2) chromatographic techniques using ion exchange, adsorption or molecular sieves; (3) electrophoresis using differential amounts of electric charges; and (4) immunoadsorption. These methods depend for their operation on the fact that the human serum albumin molecule and other protein molecules have various differences in properties such as solubility, the amount of charge and molecular size. However, the sole resource of human serum albumin is an extremely precious substance, the human blood. Additionally, the use of collected blood samples as the starting material involves the danger of contamination by serum hepatitis virus unless utmost care is exercised in the production and maintenance procedures.

Therefore, the present inventors have made various efforts to develop a stabilizer that can replace the human serum albumin and found that all of the requirements listed above are satisfied by a chemically modified gelatin (preferably, a gelatin which, after being physically modified, is decomposed and treated with diisocyanate to form urea bridges; commercially available as "Haemaccel" which contains as its principal ingredient such chemically modified gelatin with an average molecular weight of ca. 35,000). The present invention has been accomplished on the basis of this finding.

The modified gelatin used in the present invention is particularly useful as a stabilizer for the basic and labile IFN-$\gamma$. This modified gelatin is also useful for the purpose of stabilizing other physiologically active substances made of a basic protein or polypeptide. The modified gelatin is believed to be particularly effective in stabilizing those proteins or polypeptides which either assume strong basicity or become labile because of the lack of inherently attaching sugar chains, such as the proteins or polypeptides obtained from microorganisms (e.g. E. coli) by the recombinant DNA technology.

The following description of the present invention concerns human IFN-$\gamma$ for which it is particularly effective, but it should be understood that human IFN-$\gamma$ is not the only example of the physiologically active substances which are made of a basic protein or polypeptide and which are to be stabilized by the present invention.

Human interferons can be classified into three groups depending upon their antigenicity, biological properties and biochemical properties. The first group is made of leucocyte interferons ($\alpha$-interferon Le-IF or IFN-$\alpha$). The interferons in this group are principally produced by constituent cells of human blood as a result of viral induction. Alpha-interferons are also produced by genetically transformed bacteria and their biological activities have been extensively studies to such an extent that clinical use of them as therapeutics for virus diseases and malignant tumors is being promoted. The second group is comprised of human fibroblast interferons (beta-interferon, FIF or IFN-$\beta$). The interferons of this group are principally produced by fibroblasts as a result of viral induction. Beta-interferons are also produced by genetically transformed bacteria and they have been found to have a broad spectrum of biological activities. Clinical test results suggest the potential therapeutic value of beta-interferons. In spite of a relatively low degree of homology at an amino acid level, alpha- and beta-interferons have very similar biological properties.

Unlike the alpha- and beta-interferons, the human immunointerferon (gamma-interferon or IFN- ) to which the present invention is applied is labile at pH 2 and is principally produced by lymphocytes as a result of mitogenic induction. The antigenicity of IFN-$\gamma$ clearly differs from those of alpha- and beta-interferons. IFN-$\gamma$ plays an important role in the immunoregulation system and exhibits antiviral and anticyte activities which are common to all types of human interferons. Additionally, INF-$\gamma$ has synergistic effects on the activities of alpha- and beta-interferons. The in vitro activity of against the growth of malignant tumor cells is considered to be about 10 to 100 times as great as the level achieved by interferons in the other groups. In view of these effects and its impressive immunoregulating activity, IFN-γ is assumed to have far stronger antitumor activities than IFN-α and IFN-β. In fact, it has been demonstrated in in vivo tests with mouse and rat IFN-preparations that the antitumor activity of IFN-against osteosarcoma is obviously superior to that of interferons produced by induction with virus. Thus, INF-γ will possibly have immunoregulating and antitumor activities and is expected to offer an extremely effective therapeutic.

The human immunointerferon has 146 amino acid residues in its nature form whose N terminal starts with cysteine. The chemical nature of INF-γ is strong basicity. The monomeric molecular weight of INF-γ was calculated to be 17,140. Because of the presence of many basic residues, hydrophobic portions or salt bride forming radicals, the molecules of INF-γ are believed to associate with themselves in the form of oligomers, e.g. dimer, trimer and tetramer. The presence of such oligomers would be the reason why INF-γ which is a natural substance primarily produced by lymphcytes in response to mitogenic induction is observed in a high molecular weight form, and in this respect, the oligomers seem to make the same contribution as do carbohydrates produced by glycosylation after genetic translation. In any event, IFN-γ is inherently labile and prone to re-agglutination which produces aggretates with reduced biological activity. If this re-agglutination can be prevented by addition of a stabilizer, an IFN-preparation suitable for parental administration will be obtained. In accordance with the present invention, such undesired re-agglutination of IFN-γ particles can be prevented successfully.

The IFN-γ described hereinafter was obtianed from a culture of a microorganism (E. coli) created by the recombinant DNA technology (see Unexamined Published Japanese Patent Application No. 201995/1983, Japanese Patent Application Nos. 132524/1983 and 241457/1983). It should however be understood that the present invention is also applicable to IFN- that is obtained from animal cells and cell lines created by the recombinant DNA technology, as well as IFN-γ obtained from natural products such as human lymphocytes. The IFN-γ with which the present invention can be used includes the polypeptides consisting of 146 amino acid residues arranged in the same amino acid sequence as that of the human IFN-γ, as well as polypeptides that are partly deficient of the C terminal but which have IFN-γ activities, such as those used in the Examples (given later in this specification) which have 131 and 142 amino acid residues. Polypeptides having 135 amino acid residues may also be used as the IFN- in the present invention.

The chemically modified gelatin used as a stabilizer in the present invention is capable of preventing the reagglutination of IFN-γ so as to provide a preparation of physiologically active substance suitable for parenteral administration. As a further advantage, this modified gelatin is entirely free from the problems already described in connection with human serum albumin.

The chemically modified gelatin used in the present invention was originally developed as a plasma expander. Its production starts with an aqueous solution of gelatin which is rendered water soluble by spray-drying, freeze-drying or drying by radiofrequency induction heating. The so physically modified gelatin is subsequently modified by various chemical means in order to provide characteristics that suit a specific purpose. Among the chemically modified geletins used in the present invention are: oxypolygelatin prepared in 1951 by Campbell et al. (Campbell, D. A. et al., Texas Reports on Biology and Medicine, 9; 235, 1951) who condensed the physically modified gelatin with glyoxal and oxidized the resulting condensation product with hydrogen peroxide (a commercial product of this oxypolygelatin is available under the trade name "Gellifundol Biotest"); modified liquid gelatin prepared in 1952 by Tourtelotte who decomposed the physically modified gelatin and succinylated the decomposition product with succinic anhydride (the chemically modified gelatin of this type is commercially available under such trade names as Plasma Gel Logger Beron, Plasma Gel - K Brown Physiogel, and Gelafcin); and chemically modified gelatin having excellent drug resistance which was prepared in 1962 by Schmidt-Thome (Schmidt-Thome, J. et al., Arzneim. Forsch. 12; 378, 1962) who decomposed the physically modified gelatin and treated the decomposition product with diisocyanate to form urea bridges (available under the trade name "Haemaccel"). The following description concerns only the use of Haemaccel as the chemically modified gelatin.

A physically modified gelatin was prepared from fresh calf gelatin. The modified gelatin was hydrolyzed to form a polypeptide having a molecular weight of ca. 12,000 which was reacted with a diisocyanate of a suitable kind and in a suitable amount to form urea bridges, thereby producing a chemically modified gelatin of an average molecular weight of ca. 35,000 wherein three peptide chains were bound together. The physicochemical properties of the so produced chemically modified gelatin were extremely similar to those of serum globulin; viscosity, 3.7 (relative to water whose viscosity is 1).

(1) Composition in 100 ml of Haemaccel

| Components | Amounts |
|---|---|
| Chemically modified gelatin (0.63 g as nitrogen) | 3.5 g |
| Sodium chloride | 0.85 g |
| Potassium chloride | 0.038 g |
| Calcium chloride | 0.093 g |
| Distilled water for injection to make | 100 ml |

(2) Physicochemical properties

| Average molecular weight | 35,000 |
|---|---|
| Specific viscosity (35° C.) | 1.8 |
| Isoelectric point | pH 4.5–5.0 |
| pH in solution | 7.1 |
| Gel osmotic pressure | 370 mm $H_2O$ |
| Gel point | 4° C. |

Haemaccel is a pale yellow transparent liquid solution.

(3) Stability

Haemaccel remained entirely stable over a period of 3 years and 9 months in a storage test that was accompanied by temperature changes (20°–35° C.).

(4) Laboratory studies on the drug resistance, toxicity (actuate and subacute), teratogenic action, and pharmacological properties of Haemaccel, its effects on blood, blood pressure, serum and loss of electrolytes from urine, and its plasma expanding action, as well as the experience with its extensive use as a medicine in foreign countries over a period of not less than 20 years and in Japan since 1966 show that Haemaccel has the following effects and features.

1. Haemaccel has as its principal component naturally occurring proteins.
2. Haemaccel has no antigenicity.
3. Haemaccel contains electrolytes in substantially the same amounts as in the human blood plasma.
4. Haemaccel maintains blood circulation and pressure at constant levels and exhibits consistent plasma expanding effects.
5. Haemaccel may be administered repeatedly in large quantities since it is not accumulated in tissues and cause no disorders in organs.
6. Haemaccel can be used safely since it has no adverse effects on the electrolyte metabolism and hemogram.
7. Haemaccel improves edema symptoms.
8. Haemaccel is long-lived (stable against temperature changes and can be stored for no less than 1 year at room temperature, and for at least 5 year at $\leq 20°$ C.).

The first use of the chemically modified gelatin as a substitute for human serum albumin was its incorporation in the thrombolytic agent, streptokinase preparation (M. Martin and H. Auel: Anaesthesist 26, 564–568, 1977). On the basis of the results of this first use of Haemaccel, an attempt was also made to incorporate it in an immunoglobulin preparation for intravenous injection (Unexamined Published Japanese Patent Application No. 167518/1983). With this historical background and noting the fact that human serum albumin and the chemically modified gelatin have properties common to anionic polymeric proteins, the present inventors came up with the idea of using the chemically modified gelatin as a safe stabilizer that enables direct administration into the human body of IFN- exhibiting a very strong basicity and which is completely metabolized and eliminated from the human body after fulfilling its functions.

Therefore, the present invention can be applied not only to IFN-$\gamma$ but also to various other physiologically active substances made of basic proteins or polypeptides. The present invention is particularly effective for use with those proteins or polypeptides which because of the lack of inherently attaching sugar chains, assume a stronger basicity or become labile; for example, the present invention is particularly effective for use with a sugar chain free protein or polypeptide that is obtained from a transformed microorganism (e.g. $E.\ coli$) by the recombinant DNA technology.

The physiologically active substance stabilized in accordance with the present invention may be formulated in pharmaceutical preparations by mixing it with pharmaceutically acceptable expanders or excipients in accordance with any known methods.

The following examples are provided for the purpose of describing the advantages of the incorporation of the chemically modified gelatin in preparations containing IFNas the physiologically active substance. It should however be understood that these examples are for illustrative purposes only and are by no means to be constructed as limiting.

EXAMPLE 1

Three milligrams of IFN-$\gamma$ ($2\times10^8$ U/mg) was dissolved in 25 ml of 1% (and any concentration up to 3.5%) of a chemically modified gelatin (prepared by first decomposing a physically modified gelatin, and then treating the decomposition product with diisocyanate to form urea bridges; with an average molecular weight of ca. 35,000, this chemically modified gelatin is the principal component of Haemaccel), and the solution was passed through sterilization filter. The filtrate was aseptically distributed among 100 vials and aseptically freeze-fried at not higher than $+2°$ C. (preferably not higher than $-4°$ C.). The residual water content is preferably as small as possible, but as in the case of ordinary chemically modified gelatin (Unexamined Published Japanese Patent Application No. 3182/1984), a maxmum of ca. 5% is allowed for long-term storage. The vials are preferably stored at low temperature ($+2°$ C. to $+10°$ C.) until just before use. Each vial contained IFN-$\gamma$ in an amount suitable for parenteral administration ($6\times10^6$ units).

The physiologically active substance, IFN-$\gamma$, may be parenterally administered to patients who require antitumor or antiviral therapy or who are in an immunosuppressive state. The directions for use and dose of IFN-$\gamma$ may be the same as those commonly use in clinical studies of other interferons. For example, IFN-$\gamma$ may be used in a daily dose of ca. $1-10\times10^6$ units.

Examples 2 to 5 are hereunder given for the purpose of describing the advantages of addition of the chemically modified gelatin. The samples, reagents, test conditions and measurement method used in these Examples are shown below.

1. Samples (1) GIF-A (polypeptide with 146 amino acid residues arranged in the same sequence as in IFN- , produced from $E.\ coli$ created by the genetic engineering technology)
   antiviral activity: $0.9\times10^6$ U/ml.

(2) GIF-A′ (polypeptide with 142 amino acid residues on the N-terminal side arranged in the same sequence as in IFN-$\gamma$, produced from $E.\ coli$ created by the genetic engineering technology)
   antiviral activity: $0.9\times10^6$ U/ml.

(3) GIF-B (polypeptide with 131 amino acid residues on the N-terminal side arranged in the same sequence as in IFN-$\gamma$, produced from $E.\ coli$ created by the genetic engineering technology)
   antiviral activity $0.607\times10^4$ U/ml.

(4) A2 IFN (polypeptide composed of amino acid residues the same as in the amino acid sequence of IFN-$\gamma$, produced from $E.\ coli$ created by the genetic engineering technology)
   antiviral activity: $1.0\times10^6$ U/ml.

2. Diluted solutions (1) Physiological saline for injection: Lot No. K 3176T from Otsuka Pharmaceutical Co., Ltd.

(2) Tris-HCl buffers
   (2-1) 50 mM tris-HCl mixed with 10 mM EDTA-2Na (pH 7.5)
   (2-2) 20 mM tris-HCl mixed with 0.4 M NaCl and 16 mM 2-mercaptoethanol (pH 7.5)
   (2-3) 20 mM tris-HCl mixed with 0.3 M NaCl and 16 mM 2-mercaptoethanol (pH 7.5)

(3) Human albumin (fraction V): Lot No. 6617 from ICN Pharmaceuticals, prepared with physiological saline for injection to give albumin concentrations of 5%, 3.5%, 0.5% and 0.2%.

(4) Chemically modified gelatin (mol wt. 35,000) produced from Haemaccel by freeze-drying the dialyzate obtained by desalting Haemaccel daily (twice with 20 volumes of redistilled water) for 2 weeks; prepared in physiological saline for injection to give gelatin concentrations of 3.5% and 1% .

(5) Haemaccel: Lot No. 286223/5 from Farbwerke Hoechst A. G., used both as undiluted solution (3.5% chemically modified gelatin) and as 10-fold dilution (0.35% chemically modified gelatin).

3. Dilutions of samples: 1,000-fold except for GIF-B which was used as 100-fold dilution.

4. Freeze-dried or heat-dried product dissolved in: distilled water for injections (Lot No. 3A 75 from Otsuka Pharmaceutical Co., Ltd.)

5. Sterilization filter: Millex-HA, 0.45 μm, Lot No. C3S-11681.

6. Determination of antiviral activity: in accordance with the method described in "Determination of Human Interferon Titer in Terms of Inhibition of Cytopathic Effect (CPE) and by the Pigment Take-up Method", National Institute of Health, Ministry of Health and Welfare, Human cell: FL cell, Virus: Sindbis virus (both distributed by courtesy of the National Institute of Health).

EXAMPLE 2

The percent recoveries of the untreated human interferons from the filtrates obtained by passage through the sterilization filter were checked. Most of the interferons dissolved in crystalloid solutions (i.e., physiological saline for injections and tris-HCl buffers) were adsorbed on the filter; no part of GIF-A could be recovered from the filtrate, whereas GIF-A' and GIF-B could be recovered in amounts not more than 50%. When the chemically modified gelatin (3% and 1%) was added to these crystalloid solutions, the recoveries of the interferons from the filtrate were increased to as high 90–100%. The same percent recoveries were achieved by addition of the undiluted solution of Haemaccel, but considerable drop occurred with the 10-fold dilution of Haemaccel. Similarly good results were obtained with human albumin in concentrations of 3.5% and 5.0%, but it was entirely ineffective in concentrations not above 0.5%. The chemically modified gelatin was also effective in stabilizing alpha-interferon (A2-FIN).

EXAMPLE 3

The residual antiviral activities of the human interferons after freeze-drying ($\leq -20°$ C.) and any occurrence of aggregates when the freeze-dried samples were re-dissolved in distilled water were checked. The interferons dissolved in crystalloid solutions and freeze-dried had antiviral activity levels which were not more than a half of the initial levels; aggregates formed when the freeze-dried samples were re-dissolved in distilled water. When the chemically modified gelatin (3% and 1%) was added to the crystalloid solutions, the residual antiviral activities of the interferons remained as high as 90–100%, and no aggregate formed even when the freeze-dried samples were re-dissolved in distilled water. The same results were obtained by the addition of the undiluted solution of Haemaccel, but an appreciable drop in the residual antiviral activity occurred when the 10-fold dilution of Haemacell was added. Similarly good results were obtained with human albumin in concentrations of 3.5% and 5.0%, but it was entirely ineffective in concentrations not higher than 0.5%. The chemically modified gelatin was also effective in stabilizing alpha-interferon (A2-IFN).

EXAMPLE 4

The residual activiral activities of the human interferons after thermal drying ($+40°$ C.) and any occurrence of aggregates when the dried samples were re-dissolved in distilled water were checked. The interferons dissolved in crystalloid solutions and freeze-dried had no antiviral activity, and aggregates formed when the dried samples were re-dissolved in distilled water. When the chemically modified gelatin ($\geq 1\%$) was added to the crystalloid solutions, the residual antiviral activities of the interferons remained as high as 90–100%, and no aggregate formed even when the dried samples were redissolved in distilled water. The same results were obtained by addition of the undiluted solution of Haemaccel. Even human serum albumin with a concentration of 5.0% wa unable to provide residual antiviral activities exceeding 50.0%. Human albumin added in concentrations not higher than 3.5% were entirely ineffective since aggregates formed when the dried samples were re-dissolved in distilled water and the residual antiviral activities were very low. The effectiveness of the chemically modified gelatin was also confirmed in alpha-interferon (A2-IFN).

EXAMPLE 5

The time-dependent change in the percent residual antiviral activity of freeze-dried GIF-B and any occurrence of aggregates upon re-dissolution in distilled water were checked. The interferon dissolved in crystalloid solutions and freeze-dried were unable to maintain residual antiviral activity levels above 50% of the initial levels, and aggregates formed when the stored samples were re-dissolved in distilled water. When 1% chemically modified gelatin was added to the crystalloid solutions, the interferon maintained the 100% residual antiviral activity and no aggregate formed upon re-dissolution in distilled water. The interferon remained stable in the solutions containing 1% chemically modified gelatin for periods of at least about 1–2 weeks from the date of preparation.

The results of Examples 2 to 5 are summarized in the following Tables.

| Example 2: Percent Recoveries of Interferons from Sterilized and Filtered Samples | | | | | |
| --- | --- | --- | --- | --- | --- |
| Diluted sample solutions | | GIF-A | GIF-A' | GIF-B | A2-IFN |
| (dilutions) | | $0.9 \times 10^6$ U/ml | $0.9 \times 10^6$ U/ml | $0.6 \times 10^4$ U/ml | $1.0 \times 10^6$ U/ml |
| | | (1000) | (1000) | (100) | (1000) |
| Tris-HCl buffer | | 0.0 U/ml | 39.1 U/ml | 30.4 U/ml | n.d. |
| | | 0.0% | 4.3% | 50.0% | |
| | | (2-3) | (2-2) | (2-1) | |
| Human albumin | 5.0% | 900.0 U/ml | 900.0 U/ml | n.d. | n.d. |
| | | 100.0% | 100.0% | | |
| | 3.5% | 900.0 U/ml | 900.0 U/ml | n.d. | n.d. |
| | | 100.0% | 100.0% | | |
| | 1.0% | 450.0 U/ml | 900.0 U/ml | n.d. | n.d. |
| | | 50.0% | 100.0% | | |
| | 0.5% | 113.4 U/ml | 222.7 U/ml | n.d. | n.d. |

| Example 2: Percent Recoveries of Interferons from Sterilized and Filtered Samples | | | | | |
|---|---|---|---|---|---|
| | | 12.6% | 24.7% | | |
| | 0.2% | 14.2 U/ml | 56.8 U/ml | n.d. | n.d. |
| | | 1.6% | 6.3% | | |
| Chemically modified gelatin | 3.5% | 900.0 U/ml | 900.0 U/ml | 60.7 U/ml | 900.0 U/ml |
| | | 100.0% | 100.0% | 100.0% | 90.0% |
| | 1.0% | 900.0 U/ml | 900.0 U/ml | 60.7 U/ml | 900.0 U/ml |
| | | 100.0% | 100.0% | 100.0% | 90.0% |
| Undiluted Haemaccel solution (Chemically modified gelatin) | 3.5% | 900.0 U/ml | 900.0 U/ml | 60.7 U/ml | 900.0 U/ml |
| | | 100.0% | 100.0% | 100.0% | 90.0% |
| 1:10 dilution (Chemically modified gelatin) | 0.35% | 84.7 U/ml | 118.4 U/ml | n.d. | n.d. |
| | | 9.4% | 13.2% | | |

(Note)
n.d.: not determined

| Example 3: Residual Antiviral Activities of Interferons after Freeze-drying ($\leq -20°$ C.) | | | | | |
|---|---|---|---|---|---|
| Diluted sample solutions (dilutions) | | GIF-A $0.9 \times 10^6$ U/ml (1000) | GIF-A' $0.9 \times 10^6$ U/ml (1000) | GIF-B $0.6 \times 10^4$ U/ml (100) | A2-IFN $1.0 \times 10^6$ U/ml (1000) |
| Tris-HCl buffer | | 0.0 U/ml 0.0% (2-3) | 39.1 U/ml 4.3% (2-2) | 30.4 U/ml 50.0% (2-1) | n.d. |
| Human albumin | 5.0% | 900.0 U/ml 100.0% | 900.0 U/ml 100.0% | n.d. | n.d. |
| | 3.5% | 900.0 U/ml 100.0% | 900.0 U/ml 100.0% | n.d. | n.d. |
| | 1.0% | 450.0 U/ml 50.0% | 900.0 U/ml 100.0% | n.d. | n.d. |
| | 0.5% | *113.4 U/ml 12.6% | 222.7 U/ml 24.7% | *n.d. | *n.d. |
| | 0.2% | *14.2 U/ml 1.6% | *56.8 U/ml 6.3% | *n.d. | *n.d. |
| Chemically modified gelatin | 3.5% | 900.0 U/ml 100.0% | 900.0 U/ml 100.0% | 60.7 U/ml 100.0% | 900.0 U/ml 90.0% |
| | 1.0% | 900.0 U/ml 100.0% | 900.0 U/ml 100.0% | 60.7 U/ml 100.0% | 900.0 U/ml 90.0% |
| Undiluted Haemaccel solution (Chemically modified gelatin) | 3.5% | 900.0 U/ml 100.0% | 900.0 U/ml 100.0% | 60.7 U/ml 100.0% | 900.0 U/ml 90.0% |
| 1:10 dilution (Chemically modified gelatin) | 0.35% | *84.7 U/ml 9.4% | 118.4 U/ml 13.2% | n.d. | n.d. |

(Note)
n.d.: not determined
*Aggregates formed when freeze-dried samples were re-dissolved in distilled water for injection.

| Example 4: Residual Antiviral Activities of Interferons after Thermal Heating ($+40°$ C.) | | | | | |
|---|---|---|---|---|---|
| Diluted sample solutions (dilutions) | | GIF-A $0.9 \times 10^6$ U/ml (1000) | GIF-A' $0.9 \times 10^6$ U/ml (1000) | GIF-B $0.6 \times 10^4$ U/ml (100) | A2-IFN $1.0 \times 10^6$ U/ml (1000) |
| Physiological saline for injection or Tris-HCl buffer | | *0.0 U/ml 0.0% (2-3) | *0.0 U/ml 0.0% (2-2) | *0.0 U/ml 0.0% (2-1) | *0.0 U/ml 0.0% (physiological saline) |
| Human albumin | 5.0% | 450.0 U/ml 50.0% | 227.7 U/ml 24.7% | n.d. | n.d. |
| | 3.5% | *113.4 U/ml 12.6% | *56.8 U/ml 6.3% | *n.d. | *n.d. |
| | 1.0% | *14.2 U/ml 1.6% | *n.d. | *n.d. | *n.d. |
| | 0.5% | *0.0 U/ml 0.0% | *0.0 U/ml 0.0% | *n.d. | *n.d. |
| | 0.2% | *0.0 U/ml 0.0% | *0.0 U/ml 0.0% | *n.d. | *n.d. |
| Chemically modified gelatin | 3.5% | 900.0 U/ml 100.0% | 900.0 U/ml 100.0% | 60.7 U/ml 100.0% | 900.0 U/ml 90.0% |
| | 1.0% | 900.0 U/ml 100.0% | 900.0 U/ml 100.0% | 60.7 U/ml 100.0% | 900.0 U/ml 90.0% |
| Undiluted Haemaccel solution (Chemically modified gelatin) | 3.5% | 900.0 U/ml 100.0% | 900.0 U/ml 100.0% | 60.7 U/ml 100.0% | 900.0 U/ml 90.0% |
| 1:10 dilution (Chemically modified gelatin) | 0.35% | *84.7 U/ml 9.4% | 118.4 U/ml 13.2% | *n.d. | n.d. |

(Note)
n.d.: not determined
*Aggregates formed when heat-dried samples were re-dissolved in distilled water for injection.

| Example 5: Time-Dependent Change in the Residual Antiviral Activities of Freeze-Dried GIF-B | | | | |
|---|---|---|---|---|
| Days from the freeze-drying effected January 30, 1984 (The figure in parentheses denotes times of dilution) | 7 (100) | 14 (100) | 22 (100) | 35 (100) |
| Re-dissolved on the day of measurement | | | | |
| Tris-HCl buffer (2-1) | *12.5% | *12.4% | *6.6% | *3.8% |
| 1% chemically modified gelatin solution | 100.0% | 100.0% | 100.0% | 100.0% |
| Re-dissolved at day 7 from the day of freeze-drying and subsequently stored in cold place | | | | |
| Tris-HCl buffer (2-1) | *12.5% | *6.3% | *0.0% | *0.0% |
| 1% chemically modified gelatin solution | 100.0% | 100.0% | 50.0% | 25.0% |
| Non-freeze-dried solution | | | | |
| Tris-HCl buffer (2-1) | 50.0% | 50.0% | *'28.0% | *'25.0% |
| 1% chemically modified gelatin solution | 100.0% | 100.0% | 50.0% | *'25.0% |

(Note)
*Aggregates formed when the thermally dried samples were re-dissolved in distilled water for injection.
*'Aggregates formed in the solution.

What is claimed is:

1. A preparation of stabilized polypeptide having gamma-interferon activity which comprises a polypeptide having gamma-interferon activity and a modified gelatin, said gelatin having been obtained by (1) decomposing a physically modified gelatin and forming urea bridges by treatment with a diisocyanate, (2) decomposing said physically modified gelatin and succinylating the decomposition product with succinic anhydride, or (3) condensing said physically modified gelatin with glyoxal and oxidizing the condensation product with hydrogen peroxide, said physically modified gelatin being further characterized as easily water soluble and obtained by spray-drying a gelatin, freeze-drying a gelatin, or drying the same by radiofrequency induction heating.

2. A preparation according to claim 1 wherein the polypeptide is obtained from a culture of a microorganismms transformed by a recombinant DNA.

3. A preparation according to claim 2 wherein the interferon is either a polypeptide consisting of 146 amino acid residues arranged in the same amino acid sequence as that of human gamma-interferon, or a polypeptide which is partly deficient of its C terminal and which has the activity of human gamma-interferon.

4. A preparation according to claim 1 which further contains a substance selected from among an antiviral nonionic surfactant, an anionic surfactant, a human serum albumin and a sugar.

5. A preparation according to claim 4 which further contains an isotonic agent such as an inorganic salt.

* * * * *